United States Patent
Tsuchiya

(10) Patent No.: US 9,214,012 B2
(45) Date of Patent: Dec. 15, 2015

(54) APPARATUS AND METHOD FOR IMAGE PROCESSING AND STORAGE MEDIUM

(75) Inventor: Keiji Tsuchiya, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/487,004

(22) Filed: Jun. 1, 2012

(65) Prior Publication Data

US 2012/0236991 A1    Sep. 20, 2012

Related U.S. Application Data

(63) Continuation of application No. 12/403,267, filed on Mar. 12, 2009, now Pat. No. 8,213,701.

(30) Foreign Application Priority Data

Mar. 13, 2008    (JP) .................. 2008-064253

(51) Int. Cl.
*G06T 5/00*    (2006.01)
*G06K 9/40*    (2006.01)
*A61B 6/00*    (2006.01)
*H05G 1/64*    (2006.01)

(52) U.S. Cl.
CPC . *G06T 5/002* (2013.01); *A61B 6/42* (2013.01); *A61B 6/4208* (2013.01); *A61B 6/4233* (2013.01); *G06K 9/40* (2013.01); *H05G 1/64* (2013.01); *G06T 2207/10116* (2013.01); *G06T 2207/30004* (2013.01)

(58) Field of Classification Search
CPC ...... A61B 6/42; A61B 6/4208; A61B 6/4233; G06T 5/002; G06T 2207/10116; G06T 2207/30004; G06K 9/40

USPC ................. 382/132, 263, 264; 378/98.8, 207; 250/370.09

See application file for complete search history.

(56) References Cited

U.S. PATENT DOCUMENTS

| | | | |
|---|---|---|---|
| 5,003,618 A * | 3/1991 | Meno | 382/261 |
| 5,237,524 A * | 8/1993 | Heinemann | 708/322 |
| 5,319,696 A * | 6/1994 | Abdel-Malek et al. | 378/108 |
| 5,467,380 A * | 11/1995 | De Jonge et al. | 378/98.2 |
| 5,495,514 A * | 2/1996 | Horbaschek et al. | 378/98.2 |
| 5,745,542 A * | 4/1998 | Gordon et al. | 378/4 |
| 5,841,828 A * | 11/1998 | Gordon et al. | 378/4 |
| 5,949,483 A * | 9/1999 | Fossum et al. | 348/303 |
| 5,970,115 A * | 10/1999 | Colbeth et al. | 378/62 |
| 6,320,934 B1 * | 11/2001 | Carroll et al. | 378/98.8 |
| 6,404,851 B1 * | 6/2002 | Possin et al. | 378/98.7 |
| 6,404,854 B1 * | 6/2002 | Carroll et al. | 378/98.8 |
| 6,418,241 B1 * | 7/2002 | Schreiner | 382/263 |
| 6,690,493 B1 * | 2/2004 | Kobayashi et al. | 358/482 |
| 6,763,129 B1 * | 7/2004 | Honda et al. | 382/132 |

(Continued)

FOREIGN PATENT DOCUMENTS

JP    2003-204955 A    7/2003

*Primary Examiner* — Allen C. Ho
(74) *Attorney, Agent, or Firm* — Canon U.S.A., Inc. IP Division

(57) ABSTRACT

An image processing apparatus and method including executing high-pass filtering in a column direction on the pixel values of original image data read from a flat panel detector to obtain first image data, and subtracting a value obtained by converting each of the pixel values of the first image data in accordance with an absolute value of a statistic calculated from pixel values in the same pixel row of the first image data from the value of a corresponding pixel of the original image data to obtain processed image data.

37 Claims, 7 Drawing Sheets

(56) References Cited

U.S. PATENT DOCUMENTS

| | | | |
|---|---|---|---|
| 6,819,740 B2* | 11/2004 | Takahashi et al. | 378/98.8 |
| 6,829,384 B2* | 12/2004 | Schneiderman et al. | 382/154 |
| 6,904,126 B2* | 6/2005 | Endo | 378/98.8 |
| 6,952,015 B2* | 10/2005 | Kameshima | 250/370.11 |
| 7,381,963 B2* | 6/2008 | Endo et al. | 250/370.09 |
| 7,582,876 B2* | 9/2009 | Overdick et al. | 250/370.09 |
| 7,593,508 B2* | 9/2009 | Tsuchiya | 378/114 |
| 7,689,055 B2* | 3/2010 | Zhang et al. | 382/254 |
| 7,848,566 B2* | 12/2010 | Schneiderman | 382/159 |
| 7,965,333 B2* | 6/2011 | Groh et al. | 348/343 |
| 8,031,978 B2* | 10/2011 | Tamura | 382/303 |
| 8,041,092 B2* | 10/2011 | Inoue | 382/131 |
| 8,050,509 B2* | 11/2011 | Jeong et al. | 382/261 |
| 8,090,181 B2* | 1/2012 | Omi | 382/132 |
| 8,213,701 B2* | 7/2012 | Tsuchiya | 382/132 |
| 8,244,013 B2* | 8/2012 | Galant | 382/128 |
| 8,264,580 B2* | 9/2012 | Mori et al. | 348/308 |
| 8,355,594 B2* | 1/2013 | Noda | 382/260 |
| 8,374,412 B2* | 2/2013 | Kimura | 382/131 |

\* cited by examiner

APPARATUS AND METHOD FOR IMAGE PROCESSING AND STORAGE MEDIUM

CROSS-REFERENCE TO RELATED APPLICATIONS

This application is a continuation of application Ser. No. 12/403,267, U.S. Pat. No. 8,213,701, filed on Mar. 12, 2009, which claims priority from Japanese Patent Application No. 2008-064253 filed on Mar. 13, 2008, which are hereby incorporated by reference herein in their entirety.

BACKGROUND OF THE INVENTION

1. Field of the Invention

The present invention relates to a technology for reducing noise generated in an image, and in particular, to a technology for reducing noise generated in each row of an image.

2. Description of the Related Art

A known radiographic apparatus uses a flat panel detector made of amorphous silicon or polysilicon deposited or formed on a glass substrate. Original image data acquired by the flat panel detector includes noise components generated in the individual rows of an image, in addition to a pure signal component converted from incident X-rays. The flat panel detector reads the image data as an image signal by turning on and off semiconductor switches present in the same pixel row. In this case, temporal changes in gate signals for the turning on/off are considered to be one of the causes of noise generated in the individual rows of an image.

A method for reducing linear noise generated in the individual rows of an image (referred to as "horizontal noise" in Japanese Patent Laid-Open No. 2003-204955 (herein after referred to as JP-A-2003-204955)) is disclosed in JP-A-2003-204955 (FIG. 3 and so on).

The noise reducing technology described in JP-A-2003-204955 extracts noise components generated in the individual rows of an image by executing high-pass filtering in the column direction of an image and low-pass filtering in the row direction and subtracts the extracted noise components from the original image data.

However, the method described in JP-A-2003-204955 includes not only "horizontal noise" but also signal components that constitute an object. In particular, a region on the image of the object region where the values of pixels sharply changes contains the signal component of the object. Therefore, the "horizontal noise" disclosed in JP-A-2003-204955 is influenced by the acquired object image. This may cause the S/N ratio of the image signals to decrease which may be undesired.

To increase the reading speed, in general, a method for dividing a flat panel detector into multiple regions and reading image signals with different amplifiers for the individual divided regions is adopted. However, this may result in undesired noise quantity differences from one amplifier to another because of the differences in characteristic among the amplifiers.

SUMMARY OF THE INVENTION

According to an aspect of the present invention, an image processing apparatus includes a flat panel detector including a reading circuit configured to convert X-rays to original image data, a filtering device configured to execute high-pass filtering in a column direction on pixel values of the original image data to obtain first image data, and a processing unit configured to subtract a value obtained by converting the pixel values of the first image data in accordance with an absolute value of a statistic calculated from the pixel values in the same pixel row of the first image data from the values of corresponding pixels of the original image data to obtain processed image data.

Further features of the present invention will become apparent from the following description of exemplary embodiments with reference to the attached drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE EMBODIMENTS

Figure 1:
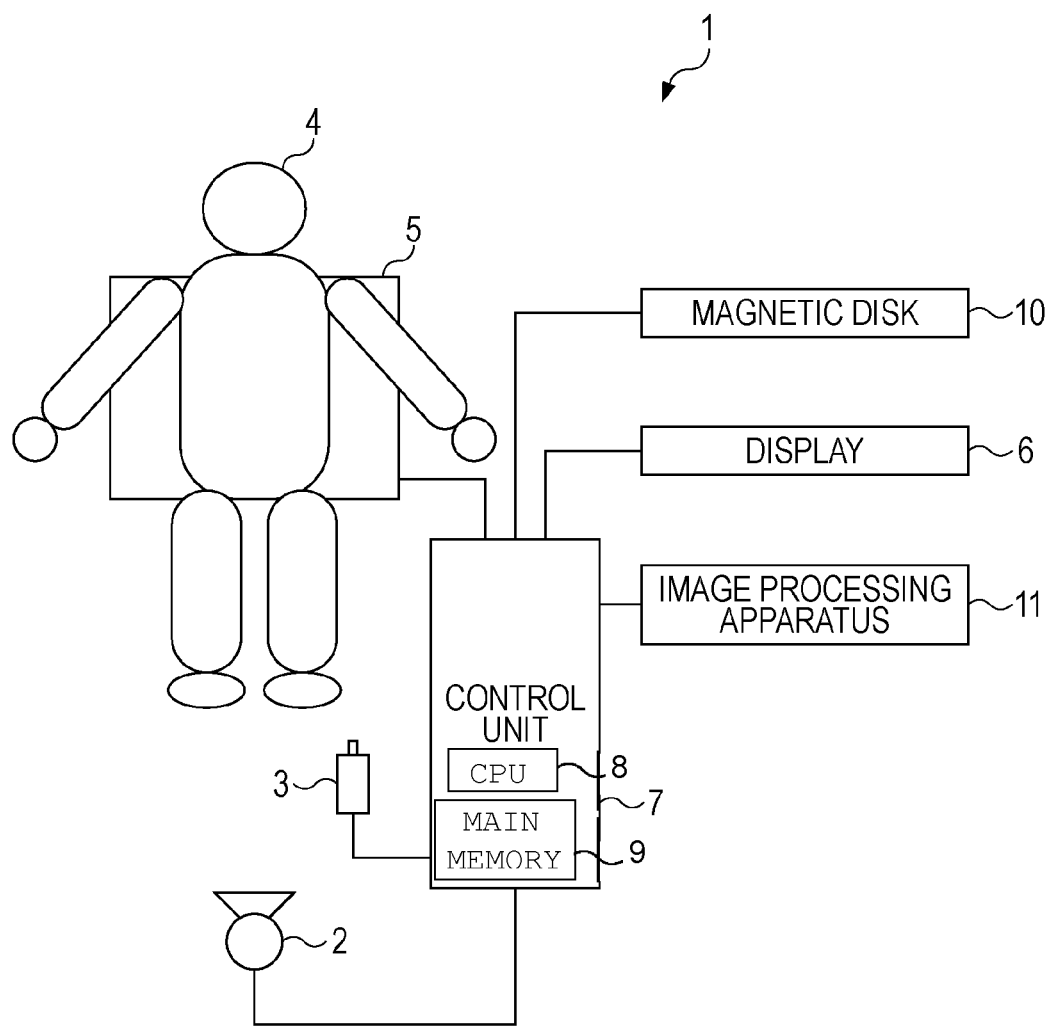
FIG. 1 is a block diagram of an image processing system according to a first embodiment of the present invention.

Exemplary embodiments of an apparatus and method for processing images according to the present invention will now be described in detail in accordance with the accompanying drawings. The scope of the invention is not limited to the examples shown in the drawings.

FIG. 1 shows a configuration example of an image processing system 1 according to a first embodiment.

An X-ray generating unit 2 exposes an object 4 to X-rays in timing at which an exposure switch 3 is pushed. The X-rays that have passed through the object 4 are acquired as original image data by a flat panel detector 5.

The flat panel detector 5 includes a plurality of pixels arrayed in a matrix form. The pixels each have a capacitor that stores an electric charge that is proportional to the amount of incident X-rays and a semiconductor switch for reading the electric charge from the capacitor.

The flat panel detector 5 includes a reading circuit. The reading circuit turns on and off the semiconductor switches in sequence for the individual rows of the matrix pixels. Electric charge taken out by turning on the semiconductor switches are read for the individual rows of the matrix pixels and converted from analog to digital, and are thus taken as digitized image signals. The values of the image signals are acquired as original image data associated with the positions of the individual pixels. That is, the original image data includes pixel values corresponding to the matrix pixels.

Since the original image data is data in which the positions of individual pixels and pixel values are associated with each other, it allows pixel values corresponding to the positions of pixels to be selected therefrom.

The image processing system 1 includes a display 6 for displaying an image based on original image data acquired by the flat panel detector 5 and a control unit 7 for controlling the whole of the image processing system 1. The control unit 7 includes a CPU 8 and a main memory 9.

The CPU 8 controls the operation of the components of the image processing system 1. The main memory 9 stores control programs that the CPU 8 executes and provides working regions during execution of the programs by the CPU 8. A magnetic disk 10 stores an operating system (OS), device drives for peripherals, various application software including programs for executing image processing etc., as described below.

Figure 2:
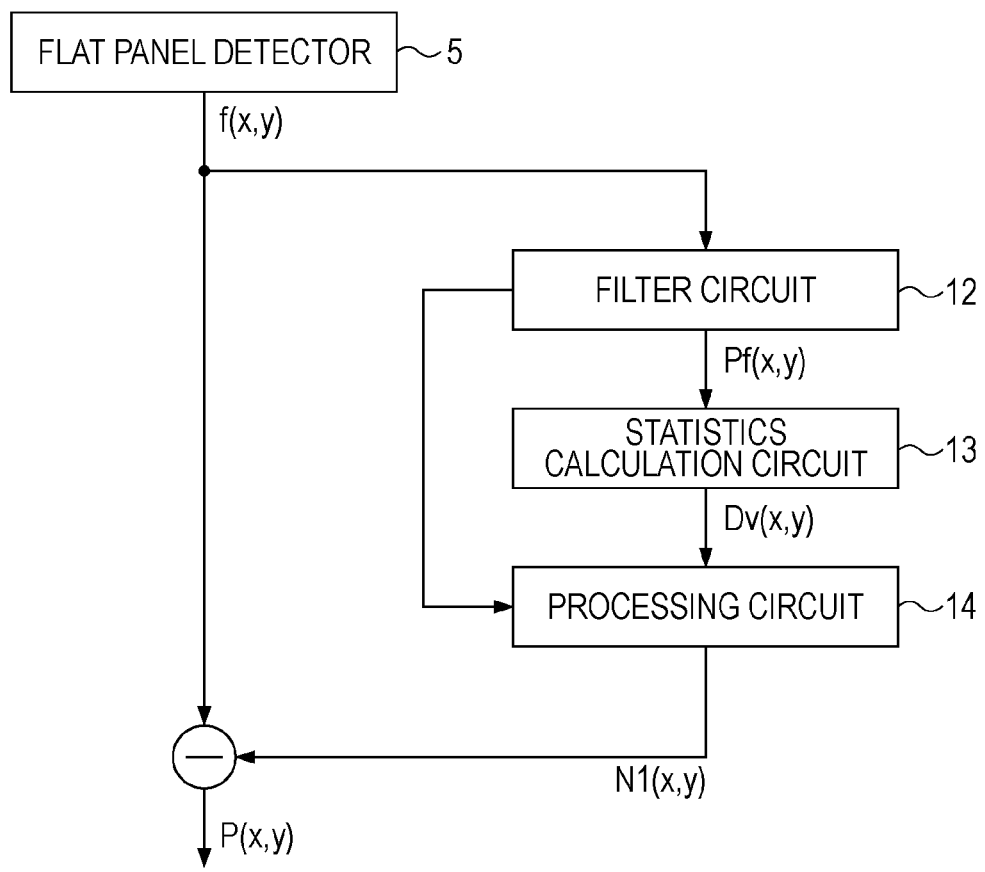
FIG. 2 is a diagram showing the circuit configuration of the image processing apparatus.

FIG. 2 is a block diagram showing the flow of data in an image processing apparatus 11.

A filter circuit 12 serving as a filtering device executes filtering of original image data f(x, y) acquired by the flat panel detector 5 to obtain filtered image data Pf(x, y).

Figure 6:
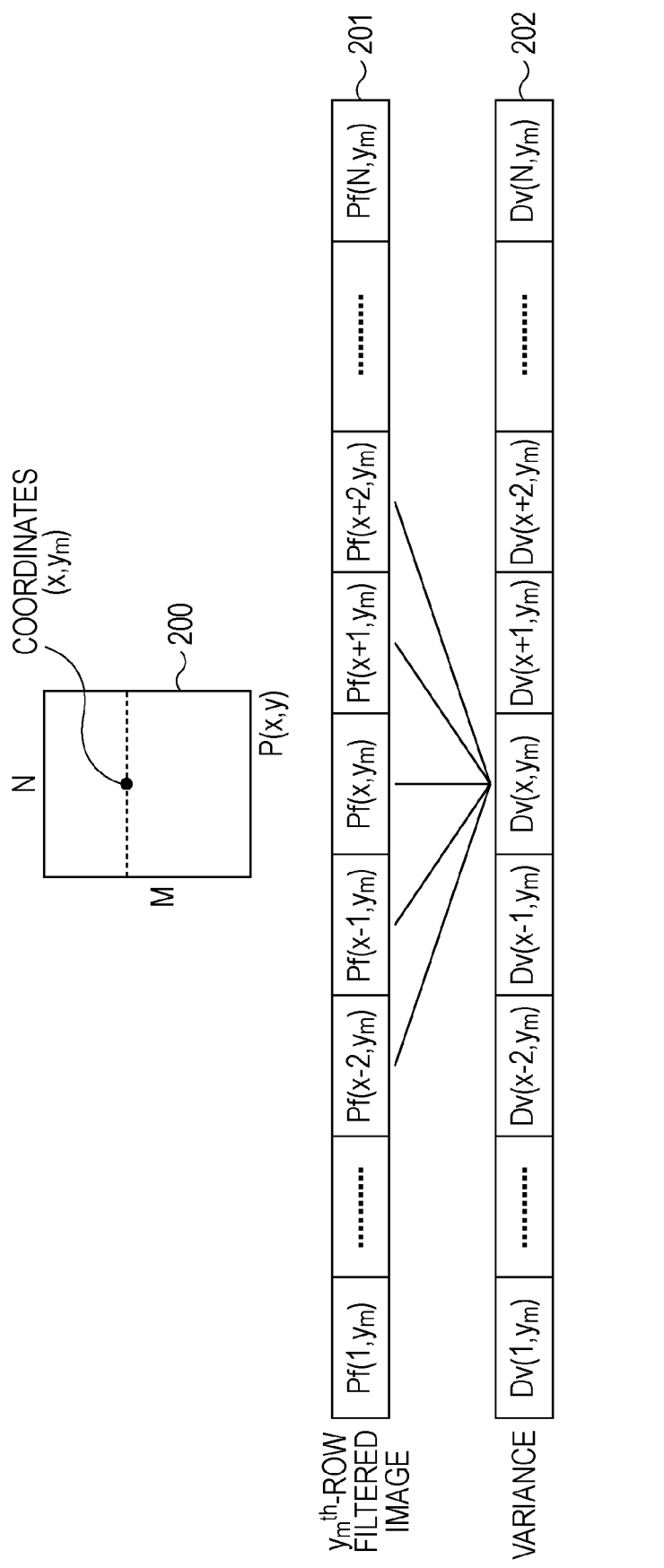
FIG. 6 is a diagram of a flat panel detector divided into three regions in the column direction.

A row direction (also referred to as "the direction of the same pixel row) in the following description indicates the direction of a pixel row in which pixels that are selected by the read circuit to read pixel signals from the pixels lie in a row. A column direction is a direction perpendicular to the pixel rows. For example, as shown in FIG. 6, for pixels arrayed in an M-row by N-column matrix, where the coordinates of a pixel is (x, y), the direction of coordinates that are selected when the value of y is set at a fixed value $y_m$ and the value of x is changed is defined as a row direction. The direction of coordinates that are selected when the value of x is fixed and the value of y is changed is defined as a vertical direction. A value f(x, y) indicate a pixel value corresponding to a pixel at coordinates (x, y).

A statistics calculation circuit 13 serving as a statistics calculating unit calculates a statistic Dv(x, y) related to noise, to be described later, from the filtered image data Pf(x, y). A processing circuit 14 serving as a processing unit calculates N1(x, y) indicating the amount of noise, calculated from the first image data Pf(x, y) on the basis of the statistic Dv(x, y), as will be described later, and subtracts the value N1 (x, y) indicating the amount of noise from the original image data f(x, y) to obtain processed image data P(x, y).

Figure 3:
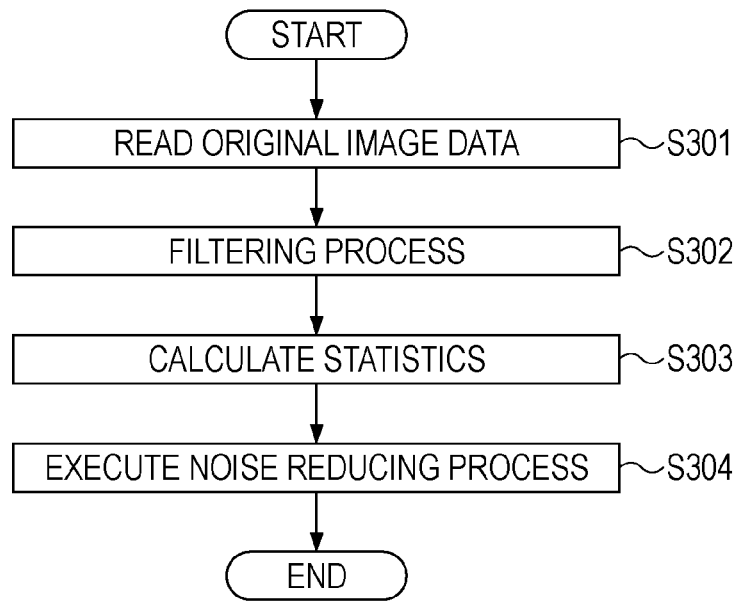
FIG. 3 is a flowchart of the process of the first embodiment.

Next, referring to the flowchart in FIG. 3, how the control unit 7 controls the image processing system 1 will be described. The process shown in FIG. 3 is implemented by the CPU 8 executing a program stored in the main memory 9.

In step S301, the CPU 8 reads the original image data f(x, y) from the flat panel detector 5. Alternatively, the CPU 8 reads original image data from a storage unit, for example, a storage medium, such as a FDD, a CD-RW drive, an MO drive, or a ZIP drive, connected to the image processing system 1.

In step S302, the CPU 8 executes the process of inputting the original image data f(x, y) to the filter circuit 12. The CPU 8 then controls the filter circuit 12 to execute high-pass filtering on the original image data f(x, y) in the column direction to obtain the first image data Pf(x, y).

Figure 4:
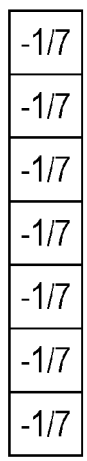
FIG. 4 is a diagram showing an example of filter factors of a column-direction filter.
Figure 5:
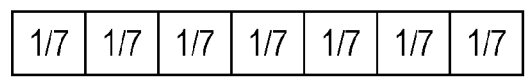
FIG. 5 is a diagram showing an example of filter factors of a row-direction filter.

FIG. 4 is a diagram showing filter factors of a column-direction high-pass filter. FIG. 5 is a diagram showing filter factors of a row-direction low-pass filter. Although the filter factor in the vertical direction and the filter factor in the horizontal direction in FIGS. 4 and 5 are 7, this is by way of example only and not limited to that particular filter factor. Although the vertical high-pass filter and the horizontal low-pass filter are FIR (finite-duration impulse response) filters, they are not limited to that; for example, they may be IIR (infinite-duration impulse response) filters.

Noise generated in the direction of pixel rows can be extracted by executing vertical high-pass filtering because the value changes from one pixel row to another.

In step S303, the CPU 8 executes the process of inputting the first image data Pf(x, y) to the statistics calculation circuit 13, and the CPU 8 controls the statistics calculation circuit 13 so as to obtain the statistics Dv (x, y) of the individual coordinates (x, y).

In step S304, the CPU 8 controls the processing circuit 14 serving as a processing unit to calculate the processed image data P(x, y).

FIG. 6 is a diagram describing acquisition of the processed image data P(x, y).

Referring to FIG. 6, reference numeral 200 denotes the first image data Pf(x, y), in which assuming that the image size of original image data is M×N, the image size of the first image data Pf(x, y) also becomes M×N. A value Pf(x, $y_m$) indicates the coordinates (x, $y_m$) of the first image data Pf(x, y), and reference numeral 201 shows a diagram in which only the values in the $y_m^{th}$ row are extracted. Reference numeral 202 shows the statistic Dv(x, $y_m$) of the $y_m^{th}$ row. The statistic Dv(x, $y_m$) is a variance calculated by using five values from Pf(x−2, $y_m$) to Pf(x+2, $y_m$), as shown in FIG. 6, for example. However, it is not limited to that and may be a statistic, such as a mean value or a standard deviation. That is, it may be a variance, a mean value, or a standard deviation calculated from the same row and is calculated from the coordinates of individual pixels on the basis of the first image data Pf(x, y) corresponding to the coordinates of pixels in a fixed region. Thus, changes in the value of pixels in the same row can be expressed as statistics of individual coordinates.

The noise component N1(x, y) of any coordinates (x, y) is calculated by the following expression [1], for example:

$$N1(x, y) = \frac{a \cdot Dm \cdot Pf(x, y)}{Dv(x, y) + Dm} \quad (1)$$

where a is a coefficient and Dm is an amount of noise of the flat panel detector 5, which is measured and stored in advance. The amount Dm that is measured and stored in advance will be described later. The value a is generally about 1. Decreasing a decreases the value N1(x, y) that indicates a noise component. If a=1 and there is no Dv(x, y), that is, no edge component, Pf(x, y) is subtracted from the original image data. Since Pf(x, y) is a value that is statistically close to Dm, a linear noise component is subtracted.

The noise component N1(x, y) can be calculated not only by Expression [1] but also by any calculation by which the absolute value of the noise component N1(x, y) decreases when the absolute value of the statistic value Dv(x, $y_m$) increases and the absolute value of the noise component N1(x, y) increases when the absolute value of the statistic value Dv(x, $y_m$) decreases.

Calculating the decrease in the absolute value of the noise component N1(x, y) in a region in which changes in pixel value in the same pixel row are large (for example, corresponding to the edge of the region of an acquired object) may result in for, example, not breaking the edge component of the object region even if the value N1(x, y) of the noise component is subtracted from the original image data f(x, y). In contrast, the absolute value of the value N1(x, y) of the noise component increases in a region in which changes in pixel value in the same pixel row are small.

The first image data Pf(x, y) may be acquired by controlling the filter circuit 12 to execute high-pass filtering in the vertical direction and low-pass filtering in the horizontal direction on the original image data f(x, y). This can decrease the value of the noise component in the same pixel row. That is, the levels of noise in the individual columns are not equal even in the same pixel row.

As described above, FIG. 5 shows an example of filter factors of a horizontal low-pass filter.

Processed image data P(x, y) is acquired by subtracting the value N1(x, y) of the noise component from the original image data f(x, y).

Next, the value Dm that is measured and stored in advance will be described. The value Dm that is measured and stored in advance is a statistic calculated from original image data that is read from the flat panel detector 5 without exposure to X-rays. The statistic is a value obtained by calculating the mean values of the original image data read from the flat panel detector 5 without exposure to X-rays for the individual horizontal rows, calculating the variance of all the mean values, and multiplying it by a coefficient.

Accordingly, the mean value Av(y) of a given $y^{th}$ row can be calculated by the following expression [2];

$$Av(y) = \frac{1}{N}\sum_{x=1}^{N} pd(x, y) \quad (2)$$

where pd(x, y) is the pixel value of an image read from the flat panel detector 5 without exposure to X-rays.

The statistic Dm that is measured and stored in advance can be calculated by the following expression [3]:

$$Dm = \frac{c}{M}\sum_{y=1}^{M} (Av(y) - \overline{Av})^2 \quad (3)$$

where c is a coefficient, and is the mean value of Av(y). Here, Dm is not limited to a variance but may be a statistic such as a mean value or a standard deviation. The time to measure Dm to be stored can be at factory shipment or at the installation of the apparatus but may not be limited to those; it may be at any time before reducing the noise. Although the value of c is generally about 3, it is not limited to that.

One of the features is that the value Dm is stored in advance and is used for determination of a noise component, as shown in Expression [1]. The value Dm is read as an image signal by the flat panel detector 5 by turning on/off semiconductor switches present in the same pixel row. In this case, temporal changes of gate signal for turning on/off are considered to be one of the causes of noise generated in the individual rows of an image.

Accordingly, when the value Dm is calculated in advance from linear noise, with no object present, a pure component caused by the temporal changes of the gate signals for turning on/off can be extracted. This allows effectively extracting only a linear noise component. It is more effective to determine the above-described value a by obtaining the amount of X-rays during exposure from the control unit 7 or the X-ray generating unit 2.

Acquisition of the value N2(x, y) of a second noise component by changing the value N1(x, y) of the first noise component will now be described. The value N2(x, y) of the second noise component is obtained by thresholding the value N1(x, y) of the first noise component and is written as the following expressions [4]:

if $N1(x, y) < b \cdot Dm$, then $N2(x, y) = b \cdot Dm$, elseif $-b \cdot Dm \leq Ni(x, y) \leq b \cdot Dm$, then $N2(x, y) = N1(x, y)$, and else, then $N2(x, y) = b \cdot Dm$ \qquad [4]

where b is a coefficient.

The value b is generally about 1. Decreasing b decreases the value N2(x, y) of the second noise component.

Figure 7:
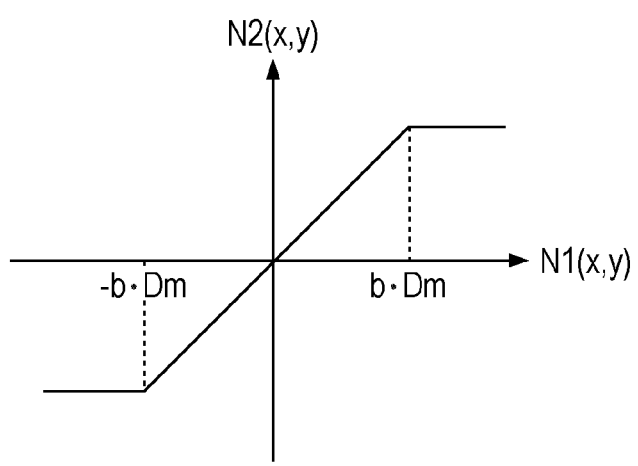
FIG. 7 is a diagram showing the relationship between filtered image data and statistics.

FIG. 7 shows the relationship between the value N1(x, y) of the first noise component and the value N2(x, y) of the second noise component. As shown in FIG. 7, when the absolute value of the value N1(x, y) of the first noise component exceeds a predetermined value, the absolute value of the value N2(x, y) of the second noise component is limited and does not increase. However, the thresholding processing is not limited to that; it is sufficient that the value N2(x, y) of the second noise component is limited when the absolute value of the value N1(x, y) of the first noise component exceeds a predetermined value. For example, the following expressions [5] are possible:

if $N1(x, y) < b \cdot Dm$, then $N2(x, y) = 0$, elseif $-b \cdot Dm \leq Ni(x, y) \leq b \cdot Dm$, then $N2(x, y) = N1(x, y)$, and else, then $N2(x, y) = 0$. \qquad [5]

In this case, the value of the second noise component is a constant.

Next, the effects of the processing will be described together with the flow thereof with reference to FIGS. 8A-8E.

Figure 8A:
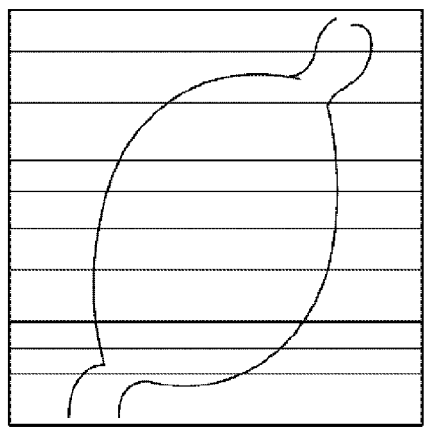
FIGS. 8A-8E are diagrams for describing the effects of the processing.

An image shown in FIG. 8A of original image data is a graphical representation of the pixel values of the original image data in which a stomach is photographed, which contains linear noise in the same pixel rows. This linear noise appears at random in the rows, and the value of the noise component also changes at random.

Figure 8B:
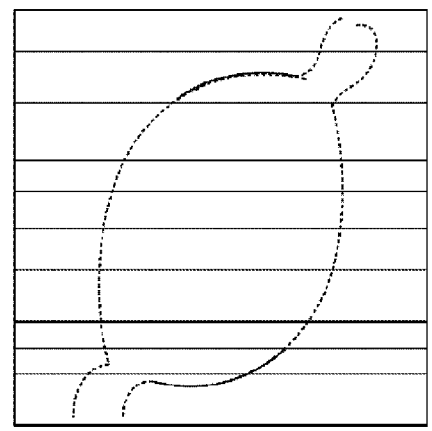

An image shown in FIG. 8B is a representation of an image of the value of the filtered image data Pf(x, y). The image shown in FIG. 8B contains a linear noise component and also an image component of the object. It particularly contains many horizontal outline components of the object.

In general, when the pixel value of displayed image data is 10 bits, the value of a linear noise component is within ±10, but the edge component of the object in filtered image data is sometimes ±110 or greater. Accordingly, when a filtered image (2) is subtracted from an original image (1), the outline of the object is influenced and is degraded in image quality.

Figure 8C:
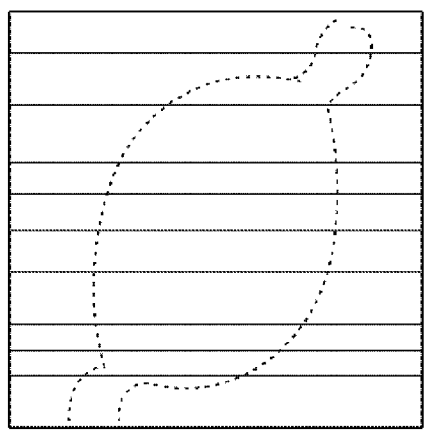

An image shown in FIG. 8C is a graphical representation of the value N1(x, y) of the first noise component. The value N1(x, y) of the first noise component is substantially the same in the same row, whereas the component of the object significantly changes at the outline of the object. Therefore, the value of the first noise component corresponding to coordinates at which the variance of filtered image data is small remains, and when the variance of the filtered image data significantly changes at the outline of the object, local variance increases. This decreases the value of the first noise component. However, the component of the object still remains in the value of the first noise component.

Figure 8D:
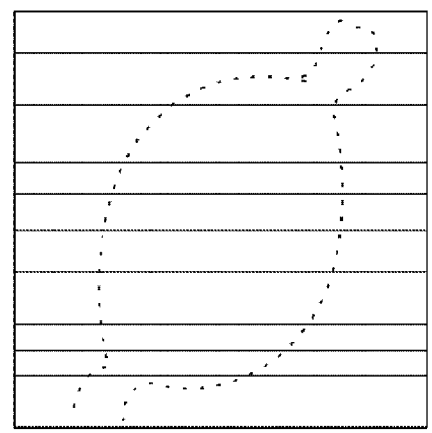

An image shown in FIG. 8D is a graphical representation of the value N2(x, y) of the second noise component. As has been described, when the value N1(x, y) of the first noise component exceeds a predetermined value, the value N2(x, y) of the second noise component is limited not to increase more. Thus, most of the components of the object are eliminated, but linear noise components remain.

Figure 8E:
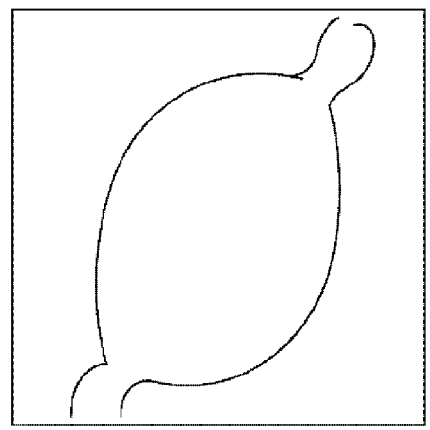

An image shown in FIG. 8E is a representation of the value of processed image data P(x, y). The second noise component is subtracted from the signal components of the object. Therefore, degradation of the image signal of the object can be reduced in the processed image data P(x, y), thus increasing the effect of reducing the linear noise. This allows processed image data, the S/N ratio of which is improved from the original image data, to be obtained. A second embodiment will now be described.

Figure 9:
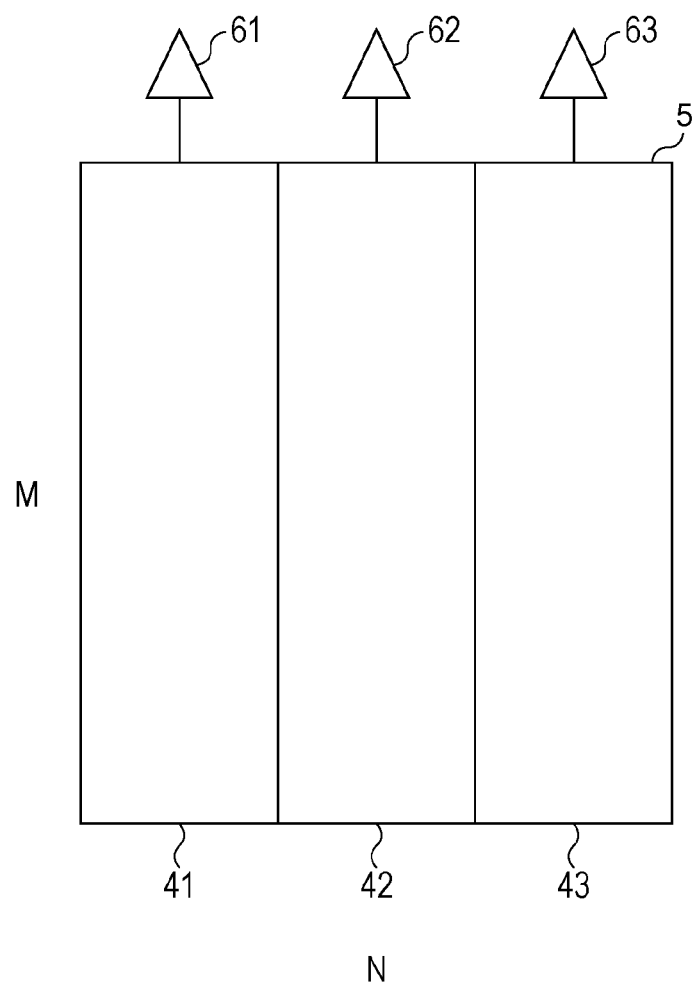
FIG. 9 is a diagram of a flat panel detector divided into three regions in the column direction.

FIG. 9 is a diagram of the flat panel detector 5 in FIG. 1 divided into three regions, that is, a region 41, a region 42, and a region 43, in the column direction to increase the reading speed. The pixels in divided region 41 are amplified by an amplifier 61, the pixels in divided region 42 are amplified by an amplifier 62, and the pixels in divided region 43 are amplified by an amplifier 63. However, the value of a linear noise component is also amplified at an amplification factor that differs from one amplifier to another because of differences in the inherent characteristics of the amplifiers. Therefore, the second embodiment performs noise reduction processing for the individual amplifiers.

To perform noise reduction processing for the individual amplifiers, the value N2(x, y) of the second noise component should be obtained for the individual amplifiers in the flowchart in FIG. 3, described above. The other processes are the same as described in the first embodiment.

Referring to FIG. 9, the value Nb2(x, y) of the second noise component in the region 41 is the mean value of the values N1(x, y) that satisfy −c·Dm or greater and c·Dm or less, where c is a coefficient.

This is written as the following expression [6]:

$$\text{if } -c \cdot Dm \leq N1(x, y) < c \cdot Dm, \text{ then } Nb2(x, y) = \text{Avr}(N1(x, y)) \quad [6]$$

where Avr(N1(x, y) indicates the mean value of N1(x, y), and Dm is the value that is obtained from the flat panel detector 5 and is measured and stored in advance, as described in the first embodiment.

The same calculation is performed on the regions 42 and 43 and values Nb2(x, y) calculated for the individual regions are subtracted from the original image to reduce the noise.

Although the present embodiment is described where the flat panel detector 5 is divided into three regions, the flat panel detector 5 can be divided into any number of regions.

The value Dm that is measured and stored in advance may be measured and stored for the individual amplifiers.

Thus, according to the present embodiment, since changes in the values of noise components caused by differences in the characteristics of amplifiers are calculated and corrected for each amplifier, noise can be reduced without degrading an X-ray image.

While the present invention has been described in detail based on the above-described embodiments, the present invention can also be embodied as, for example, a system, an apparatus, a method, a program, and a storage medium. Specifically, the present invention may be applied to a system configured by a plurality of units or an apparatus having one unit.

The present invention includes a case in which the functions of the above-described embodiments are implemented by providing a software program to a system or an apparatus directly or from a remote location and reading and executing the provided program codes by the computer of the system or the apparatus. In this case, the provided program is a computer program corresponding to the flowchart shown in FIG. 3.

Accordingly, the program codes installed in the computer to implement the functions of the present invention also achieve the present invention. In other words, the present invention includes a computer program for implementing the functions of the present invention.

In this case, the present invention may be in the form of an object code, a program implemented by an interpreter, or script data provided to an OS that has the functions of the program.

Examples of computer-readable storage media for providing the computer program are floppy disks, hard disks, optical disks, magneto-optical disks, MOs, CD-ROMs, CD-Rs, CD-RWs, magnetic tape, non-volatile memory cards, ROMs, and DVDs (DVD-ROMs and DVD-Rs).

Another method for providing the program is connecting to a website on the Internet using a browser of a client computer and downloading the computer program of the present invention from the website to a recording medium such as a hard disk. In this case, the program downloaded may be a compressed file having an automatic install function. The program codes that constitute the program of the present invention can be implemented by dividing it into more than one files and downloading the individual files from different websites. In other words, the present invention further includes a WWW server through which program files for implementing the functions of the present invention are downloaded by more than one user.

The present invention may have the form of coding the program of the present invention, storing it in a storage medium, such as a CD-ROM, and distributing it to users. In this case, the present invention may be configured to allow a user who satisfies predetermined conditions to download key information for decoding the code from a website via the Internet, to implement the coded program using the key information, and to allow a computer to install the program.

The computer executes the read program, so that the functions of the foregoing embodiments can be implemented; furthermore, the functions of the embodiments may be implemented according to an instruction of the program in cooperation with an OS or the like that is operating on the computer. In this case, the OS or the like performs part or all of the actual processing, so that the functions of the foregoing embodiments can be implemented by this processing.

Furthermore, after the program read from the storage medium is written to a function expansion board inserted into the computer or to a memory provided in a function expansion unit connected to the computer, a CPU or the like mounted on the function expansion board or function expansion unit performs all or a part of the actual processing so that the functions of the foregoing embodiments can be implemented by this processing.

The present invention can prevent noise generated in the individual rows of an image to reduce degradation of an image signal.

While the present invention has been described with reference to exemplary embodiments, it is to be understood that the invention is not limited to the disclosed exemplary embodiments. The scope of the following claims is to be accorded the broadest interpretation so as to encompass all modifications and equivalent structures and functions.

What is claimed is:

1. An image processing apparatus for reducing noise in an X-ray image obtained from a digital X-ray detector, the image processing apparatus comprising:

at least one processor and memory coupled to each other and cooperating to act as a processing unit configured to apply, to the X-ray image, a low-pass filter process in a specific direction to obtain a filtered image including pixels in the specific direction, and to extract linear noise in the specific direction from the filtered image; and a reduction unit configured to reduce noise of the X-ray image based on the extracted linear noise, wherein the processing unit is configured to perform a process for extracting the linear noise for each of segmented imaging regions of the X-ray image, the segmented imaging regions obtained by segmenting the X-ray image in the specific direction.

2. The image processing apparatus of claim 1, wherein the processing unit is configured to apply, to the X-ray image, a high-pass filter process in a direction different from the specific direction to extract the linear noise.

3. The image processing apparatus of claim 1, wherein the processing unit is configured to apply, to the X-ray image, a high-pass filter process in a direction perpendicular to a direction of the linear noise.

4. The image processing apparatus of claim 1, wherein the processing unit is configured to perform a threshold process on data based on the X-ray image, in order to extract the linear noise.

5. The image processing apparatus of claim 1, wherein the processing unit is configured to reduce an image component corresponding to an object to be imaged.

6. The image processing apparatus of claim 1, wherein the processing unit is configured to perform image processing on each of target pixels of the X-ray image, the image processing including an averaging process of a target pixel and neighboring pixels both lined in the specific direction, and a process for obtaining a value indicating a difference between a target pixel and neighboring pixels both lined in a direction different from the specific direction.

7. The image processing apparatus of claim 1,
wherein the digital X-ray detector includes amplifiers each corresponding to pixels, and
wherein the processing unit is configured to perform a process for extracting the linear noise for each of imaging regions of the X-ray image, each of the imaging regions corresponding to different one of the amplifiers.

8. The image processing apparatus of claim 7, wherein the threshold value is determined based on a value (Dm) indicating variance of values of pixels arranged in a direction perpendicular to the specific direction in two-dimensional data obtained by reading signals from the digital X-ray detector that is not irradiated with an X-ray.

9. The image processing apparatus of claim 1, wherein the processing unit is configured to extract the linear noise based on a value (Dv) indicating variance of values of pixels arranged in the specific direction in the X-ray image.

10. The image processing apparatus of claim 1, wherein the processing unit is configured to extract the linear noise based on a value (Dm) indicating variance of values of pixels arranged in a direction perpendicular to the specific direction in two-dimensional data obtained by reading signals from the digital X-ray detector that is not irradiated with an X-ray.

11. The image processing apparatus of claim 1, wherein the processing unit is configured to extract the linear noise based on a value indicating a ratio of a first value (Dv) indicating variance of values of pixels arranged in the specific direction in the X-ray image to a second value (Dm) indicating variance of values of pixels arranged in a direction perpendicular to the specific direction in two-dimensional data obtained by reading signals from the digital X-ray detector that is not irradiated with an X-ray.

12. The image processing apparatus of claim 1, wherein the processing unit is configured to extract the linear noise based on a value indicating difference between a pixel value of a target pixel in the X-ray image and pixel values of pixels neighboring the target pixel.

13. The image processing apparatus of claim 1, wherein the processing unit is configured, if a value indicating difference between a pixel value of a target pixel in the X-ray image and pixel values of pixels neighboring the target pixel exceeds a threshold value, to extract the linear noise by performing a filter process for decreasing the pixel value of the target pixel.

14. The image processing apparatus of claim 1, wherein the processing unit is configured, if a value indicating difference between a pixel value of a target pixel in the X-ray image and pixel values of pixels neighboring the target pixel exceeds a threshold value, to extract the linear noise by performing a filter process for setting the pixel value of the target pixel to zero.

15. The image processing apparatus of claim 1, wherein the low-pass filter process is an averaging process.

16. The image processing apparatus of claim 1,
wherein the processing unit is configured not to apply a low-pass filter process in a direction perpendicular to the specific direction.

17. The image processing apparatus according to claim 1, wherein after the low-pass filter process, the process for extracting the linear noise is performed.

18. An image processing apparatus for reducing noise in an X-ray image obtained from a digital X-ray detector, the image processing apparatus comprising:
a processor for:
applying, to the X-ray image, a low-pass filter process in a specific direction to obtain a filtered image including pixels in the specific direction, and to extract linear noise in the specific direction from the filtered image; and
reducing noise of the X-ray image based on the extracted linear noise,
wherein the applying further comprises extracting the linear noise for each of segmented imaging regions of the X-ray image, the segmented imaging regions obtained by segmenting the X-ray image in the specific direction.

19. An image processing system for reducing noise in an X-ray image obtained from a digital X-ray detector, the image processing system comprising:
at least one processor and memory coupled to each other and cooperating to act as a processing unit configured to apply, to the X-ray image, a low-pass filter process in a specific direction to obtain a filtered image including pixels in the specific direction, and to extract linear noise in the specific direction from the filtered image; and
a reduction unit configured to reduce noise of the X-ray image based on the extracted linear noise,
wherein the processing unit is configured to perform a process for extracting the linear noise for each of segmented imaging regions of the X-ray image, the segmented imaging regions obtained by segmenting the X-ray image in the specific direction.

20. An image processing method for reducing noise in an X-ray image obtained from a digital X-ray detector, the image processing method comprising:
storing the X-ray image in a memory;
extracting and executing the X-ray image stored in the memory using a processor;

applying, to the X-ray image, a low-pass filter process in a specific direction to obtain a filtered image including pixels in the specific direction, and to extract linear noise in the specific direction from the filtered image; and reducing noise of the X-ray image based on the extracted linear noise, wherein the processor is configured to perform a process for extracting the linear noise for each of segmented imaging regions of the X-ray image, the segmented imaging regions obtained by segmenting the X-ray image in the specific direction.

21. A non-transitory computer-readable medium storing a computer program including instructions to be executed by a computer to perform the image processing method of claim 20.

22. An image processing apparatus for an X-ray image obtained from a digital X-ray detector, the image processing apparatus comprising:

at least one processor and memory coupled to each other and cooperating to act as a processing unit configured to perform an image process on the X-ray image to obtain a data set including a plurality of items of data lined in a specific direction, the image process including, an averaging process of values of pixels of the X-ray image lined in the specific direction, and a process for obtaining a value indicating a difference between a target pixel and neighboring pixels both lined in a direction different from the specific direction; and a noise reduction unit configured to reduce linear noise of the X-ray image based on the obtained data set, wherein the processing unit is configured to perform a threshold process for an input of the value indicating the difference, in the image process to obtain the data set, and an output of the threshold process is a value whose absolute value is smaller than the value indicating the difference in a case that an absolute value of the value indicating the difference is larger than a threshold.

23. The image processing apparatus of claim 22, wherein the processing unit is configured to perform a threshold process for an input of the value indicating the difference, in the image process to obtain the data set, and the processing unit is configured to, as a result of the threshold process, output a value whose absolute value is smaller than an absolute value of the value indicating the difference in a case that the absolute value of the value indicating the difference is larger than a threshold, and output the value indicating the difference in a case that an absolute value of the value indicating the difference is smaller than the threshold.

24. The image processing apparatus of claim 22, wherein the neighboring pixels include pixels adjacent to the target pixel in a direction perpendicular to the specific direction.

25. The image processing apparatus of claim 22, wherein the processing unit is configured to perform weighted averaging of difference values of the target pixel and at least one of the neighboring pixels, to obtain the value indicating the difference.

26. The image processing apparatus of claim 22, wherein the processing unit is configured to output 0 as a result of the threshold process in a case that the absolute value of the value indicating the difference is larger than a threshold.

27. The image processing apparatus of claim 22, wherein the specific direction is one direction of a row direction and a column direction of the X-ray image and the direction different from the specific direction is the other direction.

28. The image processing apparatus of claim 22, wherein the processing unit is configured to use, as the threshold, a value based on characteristics of dark current data of the digital X-ray detector.

29. The image processing apparatus of claim 22, wherein the processing unit is configured to perform a process for extracting the linear noise for each of segmented imaging regions of the X-ray image, the segmented imaging regions obtained by segmenting the X-ray image in the predetermined direction.

30. The image processing apparatus of claim 22, wherein the digital X-ray detector includes amplifiers each corresponding to pixels, and wherein the processing unit is configured to perform a process for extracting the linear noise for each of imaging regions of the X-ray image, the imaging regions each corresponding to different one of the amplifiers.

31. The image processing apparatus of claim 22, wherein the processing unit is configured not to apply a low-pass filter process in a direction perpendicular to the specific direction.

32. An image processing apparatus for an X-ray image obtained from a digital X-ray detector, the image processing apparatus including:

at least one processor and memory coupled to each other and cooperating to perform following process comprising:

performing an image process on the X-ray image to obtain a data set including a plurality of items of data lined in a specific direction, the image process including, an averaging process of values of pixels of the X-ray image lined in the specific direction, and a process for obtaining a value indicating a difference between a target pixel and neighboring pixels both lined in a direction different from the specific direction; and reducing linear noise of the X-ray image based on the obtained data set, wherein the processor performs a threshold process for an input of the value indicating the difference, in the image process to obtain the data set, and an output of the threshold process is a value whose absolute value is smaller than the value indicating the difference in a case that an absolute value of the value indicating the difference is larger than a threshold.

33. An image processing system for an X-ray image obtained from a digital X-ray detector, the image processing system comprising:

at least one processor and memory coupled to each other and cooperating to act as a processing unit configured to perform an image process on the X-ray image to obtain a data set including a plurality of items of data lined in a specific direction, the image process including, an averaging process of values of pixels of the X-ray image lined in the specific direction, and a process for obtaining a value indicating a difference between a target pixel and neighboring pixels both lined in a direction different from the specific direction; and a noise reduction unit configured to reduce linear noise of the X-ray image based on the obtained data set, wherein the processing unit is configured to perform a threshold process for an input of the value indicating the difference, in the image process to obtain the data set, and an output of the threshold process is a value whose absolute value is smaller than the value indicating the difference in a case that an absolute value of the value indicating the difference is larger than a threshold.

34. An image processing method for an X-ray image obtained from a digital X-ray detector, the image processing method comprising:

storing the X-ray image in a memory;
extracting and executing the X-ray image stored in the memory using a processor;
performing an image process on the X-ray image to obtain a data set including a plurality of items of data lined in a specific direction, the image process including:
averaging process of values of pixels of the X-ray image lined in the specific direction, and
obtaining a value indicating a difference between a target pixel and neighboring pixels both lined in a direction different from the specific direction; and
reducing linear noise of the X-ray image based on the obtained data set,
wherein in the performing the image process to obtain the data set, performing a threshold process for an input of the value indicating the difference and outputting a value whose absolute value is smaller than the value indicating the difference in a case that an absolute value of the value indicating the difference is larger than a threshold.

35. A non-transitory computer-readable medium storing a computer program including instructions to be executed by a computer to perform the image processing method of claim 34.

36. An image processing apparatus for reducing noise in an X-ray image obtained from a digital X-ray detector, the image processing apparatus comprising:

at least one processor and memory coupled to each other and cooperating to act as a processing unit configured to apply, to the X-ray image, a low-pass filter process in a specific direction to obtain a filtered image including pixels in the specific direction, and to extract linear noise in the specific direction from the filtered image; and
a reduction unit configured to reduce noise of the X-ray image based on the extracted linear noise,
wherein the processing unit is configured to perform image processing on each of target pixels of the X-ray image, the image processing including an averaging process of a target pixel and neighboring pixels both lined in the specific direction, and a process for obtaining a value indicating a difference between a target pixel and neighboring pixels both lined in a direction different from the specific direction.

37. An image processing apparatus for reducing noise in an X-ray image obtained from a digital X-ray detector, the image processing apparatus comprising:

at least one processor and memory coupled to each other and cooperating to act as a processing unit configured to apply, to the X-ray image, a low-pass filter process in a specific direction to obtain a filtered image including pixels in the specific direction, and to extract linear noise in the specific direction from the filtered image; and
a reduction unit configured to reduce noise of the X-ray image based on the extracted linear noise,
wherein the processing unit is configured to perform a process for extracting the linear noise for each of segmented imaging regions of the X-ray image, the segmented imaging regions obtained by segmenting the X-ray image in the specific direction, and to extract the linear noise based on a value indicating difference between a pixel value of a target pixel in the X-ray image and pixel values of pixels neighboring the target pixel.

* * * * *